United States Patent
Limaye et al.

(10) Patent No.: US 11,890,088 B2
(45) Date of Patent: Feb. 6, 2024

(54) CANNULA INSERTION DETECTION

(71) Applicant: Becton, Dickinson and Company, Franklin Lakes, NJ (US)

(72) Inventors: Amit Limaye, Wayne, NJ (US); Keith Knapp, Warwick, NY (US); Elizabeth Nelson, Wellesley, MA (US); Patrick Allen, Needham, MA (US); Amanda Masotta, Cohasset, MA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 17/955,146

(22) Filed: Sep. 28, 2022

(65) Prior Publication Data
US 2023/0016823 A1    Jan. 19, 2023

Related U.S. Application Data

(62) Division of application No. 15/845,999, filed on Dec. 18, 2017, now Pat. No. 11,490,831, which is a
(Continued)

(51) Int. Cl.
*A61B 5/06* (2006.01)
*A61M 5/142* (2006.01)
(Continued)

(52) U.S. Cl.
CPC ............ *A61B 5/063* (2013.01); *A61B 5/0004* (2013.01); *A61B 5/0531* (2013.01); *A61B 5/062* (2013.01); *A61B 5/14503* (2013.01); *A61B 5/14532* (2013.01); *A61B 5/157* (2013.01); *A61B 5/15109* (2013.01); *A61B 5/742* (2013.01); *A61B 5/7405* (2013.01); *A61B 5/746* (2013.01); *A61B 5/7455* (2013.01);
(Continued)

(58) Field of Classification Search
None
See application file for complete search history.

(56) References Cited

U.S. PATENT DOCUMENTS 4,535,773 A * 8/1985 Yoon .................. A61B 17/3496
604/118
5,571,133 A    11/1996 Yoon
(Continued)

FOREIGN PATENT DOCUMENTS

AU    738918 B2    9/2001
EP    1987761 A1    11/2008
(Continued)

OTHER PUBLICATIONS

Japanese Office Action dated Feb. 2, 2021, which issued in the corresponding Japanese Patent Application No. 2020-025442, including English translation.
(Continued)

*Primary Examiner* — Jacqueline Cheng
*Assistant Examiner* — Jairo H Portillo
(74) *Attorney, Agent, or Firm* — Dickinson Wright PLLC

(57) ABSTRACT

Sensors are disclosed that detect whether a cannula is properly inserted to its full depth in a subject's skin. The sensors may be used with a blood glucose monitor, or with a continuous insulin infusion pump, infusion set, or other system involving intermittent or continuous testing and/or drug delivery.

8 Claims, 5 Drawing Sheets

Related U.S. Application Data division of application No. 14/499,517, filed on Sep. 29, 2014, now Pat. No. 9,872,633.

(51) Int. Cl.

| | |
|---|---|
| *A61B 34/20* | (2016.01) |
| *A61M 5/46* | (2006.01) |
| *A61B 5/00* | (2006.01) |
| *A61B 5/0531* | (2021.01) |
| *A61B 5/145* | (2006.01) |
| *A61B 5/151* | (2006.01) |
| *A61B 5/157* | (2006.01) |
| *A61B 17/34* | (2006.01) |
| *A61M 5/158* | (2006.01) |
| *A61M 25/01* | (2006.01) |
| *A61B 90/00* | (2016.01) |
| *A61M 5/20* | (2006.01) |

(52) U.S. Cl.
CPC .......... *A61B 17/3403* (2013.01); *A61B 34/20* (2016.02); *A61B 90/36* (2016.02); *A61B 90/39* (2016.02); *A61M 5/14248* (2013.01); *A61M 5/158* (2013.01); *A61M 5/46* (2013.01); *A61M 25/0127* (2013.01); *A61B 2034/2055* (2016.02); *A61B 2090/373* (2016.02); *A61B 2090/3904* (2016.02); *A61M 2005/14252* (2013.01); *A61M 2005/1585* (2013.01); *A61M 2005/1588* (2013.01); *A61M 2005/208* (2013.01); *A61M 2025/0166* (2013.01); *A61M 2205/13* (2013.01); *A61M 2205/3317* (2013.01); *A61M 2205/581* (2013.01); *A61M 2205/582* (2013.01); *A61M 2205/583* (2013.01)

(56) References Cited

U.S. PATENT DOCUMENTS

| | | | |
|---|---|---|---|
| 5,632,730 A | 5/1997 | Reinert | |
| 6,093,172 A | 7/2000 | Funderburk | |
| 6,767,336 B1 | 7/2004 | Kaplan | |
| 7,713,258 B2 | 5/2010 | Adams et al. | |
| 2002/0183738 A1 | 12/2002 | Chee | |
| 2003/0045802 A1 | 3/2003 | Kato | |
| 2003/0120297 A1 | 6/2003 | Beyerlein | |
| 2003/0236502 A1 | 12/2003 | De La Serna et al. | |
| 2005/0004513 A1 | 1/2005 | Beyerlein | |
| 2006/0258929 A1 | 11/2006 | Goode, Jr. | |
| 2007/0027381 A1 | 2/2007 | Stafford | |
| 2008/0039914 A1 | 2/2008 | Cory | |
| 2008/0294096 A1* | 11/2008 | Uber, III | A61M 31/005 604/66 |
| 2009/0099521 A1 | 4/2009 | Gravesen et al. | |
| 2009/0130639 A1 | 5/2009 | Skinner | |
| 2009/0221890 A1 | 9/2009 | Saffer et al. | |
| 2010/0137695 A1* | 6/2010 | Yodfat | A61B 5/6849 604/272 |
| 2010/0160902 A1 | 6/2010 | Aeschilimann et al. | |
| 2010/0286507 A1 | 11/2010 | Paassilta | |
| 2011/0105942 A1 | 5/2011 | Lim | |
| 2011/0160675 A1* | 6/2011 | Ruan | A61M 5/3272 604/198 |
| 2012/0302873 A1 | 11/2012 | Tajima | |
| 2012/0310157 A1 | 12/2012 | Ishikawa et al. | |
| 2014/0039451 A1 | 2/2014 | Gangera et al. | |
| 2014/0128815 A1 | 5/2014 | Cabiri et al. | |
| 2014/0272861 A1 | 9/2014 | Bergman et al. | |
| 2015/0234248 A1 | 8/2015 | Ram et al. | |
| 2016/0081712 A1* | 3/2016 | Heniford | A61B 90/37 600/424 |

FOREIGN PATENT DOCUMENTS

| | | |
|---|---|---|
| EP | 2198778 A1 | 6/2010 |
| EP | 2340070 A1 | 7/2011 |
| EP | 2703029 A1 | 3/2014 |
| JP | Sho 56-83360 A | 7/1981 |
| JP | 2001-513371 A1 | 9/2001 |
| JP | 2003505159 | 2/2003 |
| JP | 2004-290583 A | 10/2004 |
| JP | 2010240311 | 10/2010 |
| JP | 2011-507648 A | 3/2011 |
| JP | 2014510573 | 5/2014 |
| JP | 2014510574 | 5/2014 |
| JP | 2014176455 | 9/2014 |
| WO | 1999/007425 A1 | 2/1999 |
| WO | WO-0240083 A2 | 5/2002 |
| WO | WO-03080169 A1 | 10/2003 |
| WO | WO-03090509 A2 | 11/2003 |
| WO | WO-2006067217 A2 | 6/2006 |
| WO | WO-2006124759 A2 | 11/2006 |
| WO | 2009/083651 A1 | 7/2009 |
| WO | 2007108519 | 8/2009 |
| WO | WO-2010125551 A2 | 11/2010 |
| WO | WO-2011068741 A1 | 6/2011 |
| WO | 2014/037322 A1 | 3/2014 |
| WO | WO-2014066256 A1 | 5/2014 |
| WO | WO-2014116998 A2 | 7/2014 |
| WO | 2014/143815 A2 | 9/2014 |
| WO | 2014143815 | 9/2014 |

OTHER PUBLICATIONS

Japanese Office Action dated Jan. 26, 2021, which issued in the corresponding Japanese Patent Application No. 2020-025440, including English translation.

Japanese Office Action dated Jan. 26, 2021, which issued in the corresponding Japanese Patent Application No. 2020-025441, including English translation.

\* cited by examiner

CANNULA INSERTION DETECTION

This application is a division of U.S. patent application Ser. No. 15/845,999, filed on Dec. 18, 2017, which is a division of U.S. patent application Ser. No. 14/499,517, filed on Sep. 29, 2014, now U.S. Pat. No. 9,872,633 issued on Jan. 23, 2018, which are incorporated herein by reference in their entireties.

FIELD OF THE INVENTION

The invention is in the field of medical devices. Specifically the invention is directed to methods and apparatus for automatically detecting whether a percutaneous medication delivery device such as a cannula or catheter or a diagnostic device such as a sensor is fully inserted at an insertion site on a user's body. The invention may be used with a blood testing device, such as a blood glucose monitor, or medication delivery device, such as an insulin infusion pump or patch, but is not limited to such devices.

BACKGROUND OF THE INVENTION

A blood testing or medication delivery device worn on the body must have a cannula, catheter or probe properly inserted into the patient's skin to operate. Incomplete insertion may result from flexing or tenting of the skin, from incomplete insertion by the user or separation of the device from the body during use. Such devices often do not have a mechanism that enables confirmation that the delivery device is properly inserted.

As an example of a medication delivery device known in the prior art, U.S. Pat. No. 8,475,432, which is incorporated by reference, describes a medication delivery device worn on the body having an automated cannula insertion mechanism. U.S. Pat. No. 8,603,075 describes an electrochemical blood glucose probe which may be part of an apparatus worn on the body and is likewise incorporated by reference for its description of sensor/probe technology.

Percutaneous injections may be performed in the intradermal (ID) region, the subcutaneous (SC) region and the intramuscular (IM) region. For many types of injectable medications, including insulin, the SC region is preferred for administering an injection because of the blood flow through the fatty layer of the subcutaneous region. See, for example, Lo Presti, et al., Skin and subcutaneous thickness at injecting sites in children with diabetes: ultrasound findings and recommendations for giving injection, *Pediatric Diabetes* (2012). Alternatively, an injection may also be administered into the dermal layer. Many medication delivery devices cannot reliably ensure delivery to the SC region because of improper insertion.

If a cannula, catheter or probe is oriented at an angle with respect to the user's skin, the tip of the device may fail to reach the desired SC space after insertion.

In-vivo monitoring of blood glucose levels and the like is typically done using probes attached to an on body sensor (OBS) attached to a cannula, catheter or a probe, worn on the user's body and inserted into the user's skin at an insertion site. The ability of the probe to detect in the region of interest is greatly enabled or disabled by the ability of the user to place it in the intended location. Inserting and maintaining the probe in the desired location can often be unreliable, and users are likely to use different practices which adds to the unreliability. Installation often requires two-handed operation and can cause discomfort. Likewise, the different commercially available systems for the automatic delivery of medication, such as insulin patch pumps and infusion sets, in which a cannula is required to be inserted for continuous drug delivery, generally lack simple and reliable device feedback when the cannula is incorrectly inserted or seated at the insertion point.

SUMMARY OF THE INVENTION

In view of the problems identified in the prior art, one object of the invention is to provide an injection depth sensor in a device where the cannula, catheter or probe is worn on the body. Another object of the invention is to ensure that a cannula, catheter or probe reaches the proper insertion depth. A further object of the invention is to provide a simpler mechanism for reliable insertion and detection of a cannula, catheter or probe. Yet a further object of the invention is to alert a user if a cannula, catheter or probe is oriented at an angle. These and other objects of the invention are achieved with insertion monitors and methods of using as shown and described below.

In one aspect, the invention is an insertion monitor, comprising a housing having a top and a base adapted to be positioned adjacent an insertion site on a subject's skin. The cannula, catheter or probe, as the case may be, has a distal end with a bevel adapted for insertion into a subject's skin, and a proximal end within the housing. A pair of electrical contacts in a central area of the base of the housing proximate the cannula, catheter or probe contact the subject's skin when the cannula, catheter or probe has reached full penetration depth. A sensor circuit including the pair of electrical contacts detects a change in an electrical property in the sensor circuit when the electrical contacts make contact with the subject's skin, and when contact is interrupted, which triggers an alert mechanism responsive to the change in electrical property to provide indication of the cannula insertion status.

In a further aspect of the invention, an insertion monitor according to the invention provides sensors on opposite sides of the cannula, catheter or probe to detect whether the cannula, catheter or probe is oriented at an angle at the injection site, which can detect or prevent improper insertion. Additional sensors (i.e., a total of three, four or more sensors) may be used to determine whether angled insertion has occurred, and the sensors need not be positioned opposite each other to make a determination regarding insertion status.

In another aspect, an insertion monitor according to the invention utilizes a pair of mechanical posts as the insertion indicator mechanism. In this aspect, the invention comprises a housing having a top and a base adapted to be positioned on a subject's skin adjacent an insertion site. The cannula, catheter or probe has a distal end with a bevel adapted for insertion into the subject's skin protruding distally from the base and a proximal end within the housing. At least a pair of mechanical posts is provided having a respective distal end protruding distally from the base in a central area of the base proximate the cannula, catheter or probe, and a respective proximal end within the housing. The posts traveling proximally within the housing in correspondence with insertion of the cannula into the subject's skin provides an indication of the cannula, catheter or probe insertion status. The indication may be a signal transmitted to remote device, such as a monitor or medication delivery device, or a visible, audible and/or tactile indication on the device housing. A "remote device" may include a smart phone, or tablet, or the like. A "remote medication source" is also understood to include a conventional tube pump controller and a wireless pump controller.

In other embodiments, a pair of mechanical posts is provided on opposite sides of the cannula, catheter or probe, and an indication of angled insertion is generated when one of the pair of mechanical posts moves a greater distance proximally in the housing than the other of the pair.

In a further aspect of the invention, an insertion monitor according to the invention may utilize a spring loaded collar received in the device housing and surrounding the cannula, catheter or probe. In this aspect, the invention comprises a housing adapted to be positioned on a subject's skin adjacent an insertion site, having a recess receiving a spring loaded collar surrounding a cannula, catheter or probe. The cannula, catheter, or probe has a distal end with a bevel and a proximal end. The spring loaded collar comprises a collar surrounding the cannula, catheter or probe, and a spring positioned between the recess in the housing and the collar. A sensor detects when the spring loaded collar is seated fully in the recess in the housing with a distal surface of the collar in a plane with the distal surface of the housing and triggers an alert mechanism indicating the insertion status.

In a further aspect of the invention, one or more electrodes is placed on the cannula itself to detect an electrical property of the subject's tissue at the injection site to monitor injection status. This may involve two electrodes positioned on an insulating layer on the cannula, detecting current between the electrodes or other electrical property. Alternatively, the cannula itself provides an electrical contact, and another contact is placed on the base of the housing proximate the injection site, as in the first aspect of the invention described above.

For example, and not by way of limitation, a cannula insertion monitor according to one of these embodiments comprises: a cannula having a distal end with a bevel and a proximal end positioned in a housing, an electrically insulating layer on the cannula, an electrically conductive distal electrode on the insulating layer and an electrically conductive proximal electrode positioned proximally of the distal electrode on the insulating layer. The housing is adapted to be positioned against a subject's skin and includes a sensor circuit electrically connected with the distal electrode and the proximal electrode to detect a change in electrical property between said distal electrode and said proximal electrode. An alert mechanism responsive to the detected change in electrical property provides an indication of insertion status.

Figure 1:
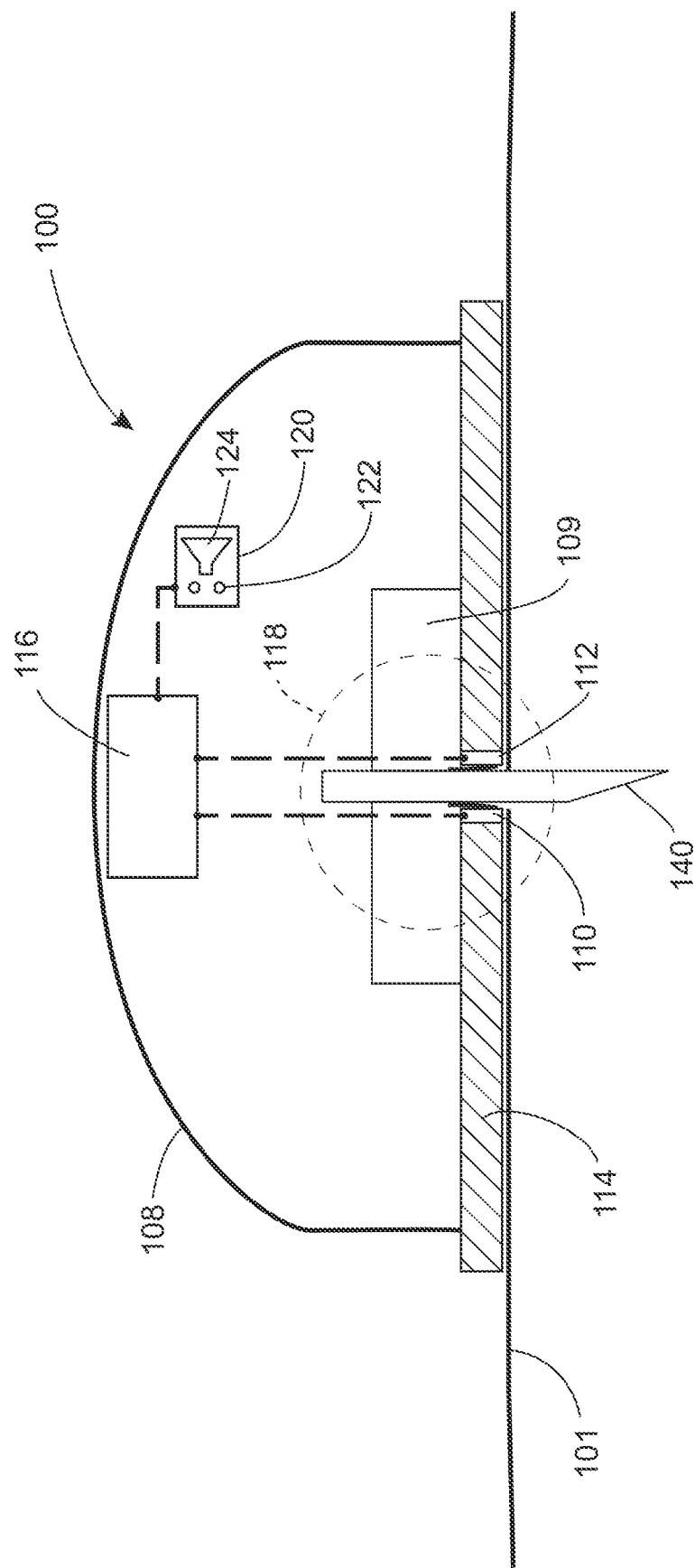
FIG. 1 depicts an insertion monitor according to an embodiment of the invention wherein electrical contacts at the insertion site are connected to a sensor circuit to monitor whether the cannula is properly inserted.

The Figures are schematic only and are not drawn to scale.

DETAILED DESCRIPTION OF THE INVENTION

The present invention is useful in any medication delivery, sensing and/or testing application having an inserted or in-dwelling delivery device or probe worn by the user. For example, and not by way of limitation, "medication delivery" includes an infusion pump attached to a patch by tubing, wherein the patch is attached to the user's body via a plastic catheter. Plastic catheters for infusion often have insertion needles within, where the cutting bevel is located. In that case, the invention is used to ensure that the catheter is properly seated. Alternatively, an infusion device may insert a metal cannula directly into the skin for medication delivery, without using a catheter. Similarly, a sensing device for blood testing may utilize a catheter to enclose a probe (in which case the insertion monitor detects the insertion status of the catheter), or a probe may be inserted directly into the skin (in which case the insertion monitor detects the insertion status of the probe itself). Many glucose monitoring sensors have an insertion needle (called an "over-needle") that provides the cutting bevel; the over needle is withdrawn from the patient after the initial incision. In all of these embodiments, the insertion detection provides the user with an indication that the sensor or probe is properly inserted and ready to perform its function. As used herein, disclosure relating to insertion detection for a "cannula" is understood to apply equally well to a catheter or probe.

As used herein, the "distal" direction is in the direction of the cannula insertion, and the "proximal direction" is the opposite direction. Certain insertion monitors according to the invention provide visible, and/or audible and/or tactile indication of "cannula insertion status," meaning that (i) the cannula is fully inserted and ready for use with an associated device; or (ii) the cannula is not fully inserted and is not ready for use. Depending on the embodiment, the monitor may provide an indication of ready status (i), not-ready status (ii), or both (i) and (ii). Alternatively, or in addition, an indication of cannula insertion status may be transmitted to other components within the device, to initiate or stop drug delivery or blood testing, for example, without providing a visible, audible and/or tactile result to the user. A "tactile" indication includes a vibration mode.

The insertion monitor of the invention may be used with any system where a cannula, catheter or probe is inserted into the skin for a period of time, including without limitation, a blood glucose monitor, an insulin infusion set or an on-body infusion pump. These systems may have an automatic insertion mechanism on a housing proximate the injection site, which may be activated remotely via the insertion mechanism, or the cannula may be inserted manually by the user. A probe may be provided with reagents and electrical contacts for the electrochemical determination of blood glucose, as known in the art.

FIG. 1 depicts an embodiment of the insertion monitor 100 wherein electrical contacts 110, 112 are provided in an area around central portion 118 of the sensor 100, i.e., proximate cannula 140, which is supported on hub 109. In this embodiment, base 114 of the housing is positioned flush against the skin when cannula 140 is fully inserted. The base may be flexible and provided with adhesive in some embodiments to adhere and conform to the skin. Electrical contacts 110 and 112 are positioned close enough to cannula 140 that both contacts 110, 112 touch the subject's skin when cannula 140 is inserted, but fail to make contact when the skin is tented. Tenting of the skin may occur when cannula 140 pushes the skin distally instead of penetrating fully into the targeted subcutaneous space, as may result when the cannula or catheter, as the case may be, encounters a local hard area of skin or hair follicle for example. As shown in the different embodiment of FIG. 3C, tenting creates an area of skin adjacent the cannula not in contact with the base of the device. When the skin 101 is pushed away from base 114 of the device, contacts 110 and 112 should register a contact failure. For this purpose, the contacts may be located substantially adjacent the cannula or catheter as the case may be, up to a distance of about 12 mm. A distance greater than 12 mm fails to register the likelihood of a shallow injection due to insufficient penetration depth of the cannula due to tenting. A cannula is shown in FIG. 1, but the person of ordinary skill in the art will appreciate that many catheters for infusion have insertion needles within, in which case the insertion monitor would typically be provided with respect to the catheter, to provide insertion status of the catheter.

When both electrical contacts 110, 112 make contact with the skin, the sensor circuit detects a change in electrical property in the sensor circuit 116, typically an increase in capacitance. Touch sensitive devices are known in the art in which an electrode in the device acts as the charge plate of a capacitor, and when a user's body is brought into proximity with the electrode, a virtual capacitor is formed, with the body acting as the second capacitor plate. Capacitance may be measured using a capacitance-to-digital converter (CDC). This technology, already being used in the healthcare context, may be readily adapted for use with an injection depth sensor according to the invention, with electrical contacts 110, 112 connected in a sensor circuit 116 to measure an electrical property that changes when the electrical contacts come into contact with the user's skin. Although described in terms of capacitance, the person of ordinary skill in the art will recognize that the skin has other electrical properties that may be leveraged to make this measurement. Thus, another electrical property, such as resistance, impedance or conductivity, could be measured to determine whether proper contact is made between the electrodes 110, 112 and the skin at the injection site. In general, an electrical property may be measured in two ways, where the skin is directly contacted, and where sensing electrodes approach but do not touch the skin. A capacitance change can be measured without skin contact, whereas measuring a change in resistance requires skin contact. In addition to the pair of electrical contacts 110, 112, additional electrode point sensors may be included proximate the area of the insertion.

Sensor circuit 116 generates a signal in response to the change in electrical property which is transmitted to alert mechanism 120, which may be in the form of one or more visible lights, such as light emitting diode (LED) 122, one or more audible alarms 124, or a combination of LED and audible alarm. Alert mechanism 120 may create a sensible vibration. Alternatively, the sensor circuit 116 may provide the indication of cannula insertion status to a remote testing or delivery device. Likewise, an interruption in skin contact, as may be caused by a change in the skin condition, caused by tenting or flexing for example, or by base 114 of housing 108 pulling away from the skin 101, causes a different signal to be transmitted by the sensor circuit, communicating to the user, or to the device, that cannula insertion is in a failure condition. In a simple example, a red LED indicates that the cannula is not properly inserted, and a green LED indicates that the cannula is properly inserted. Alternatively, or in addition, cannula insertion status may be transmitted to a peripheral device such as a blood glucose monitor or infusion pump.

Angled insertion of a cannula, catheter or probe is undesirable because the tip of the cannula, catheter or probe may not reach the desired subcutaneous space. The insertion monitor having two contacts proximate the injection site permits detection of angled insertion. For example, when one of the pair of electrical contacts is in contact with the subject's skin and the other is not, the monitor may trigger an alert mechanism to indicate angled insertion. This will prompt the user to fix the angle or prompt a peripheral device to appropriate action, such as stopping infusion or testing.

Figure 2A:
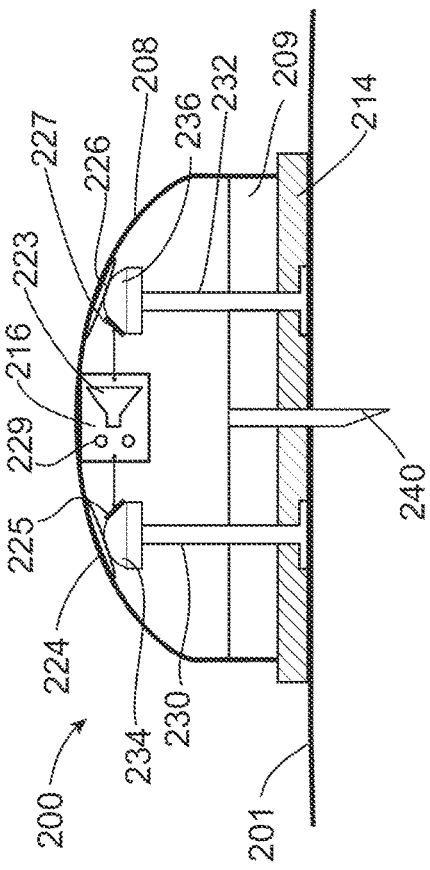
FIG. 2A, FIG. 2B, FIG. 2C and FIG. 2D depict an insertion monitor according to two other embodiments of the invention, utilizing a pair of mechanical posts proximate the cannula insertion site.
Figure 2B:
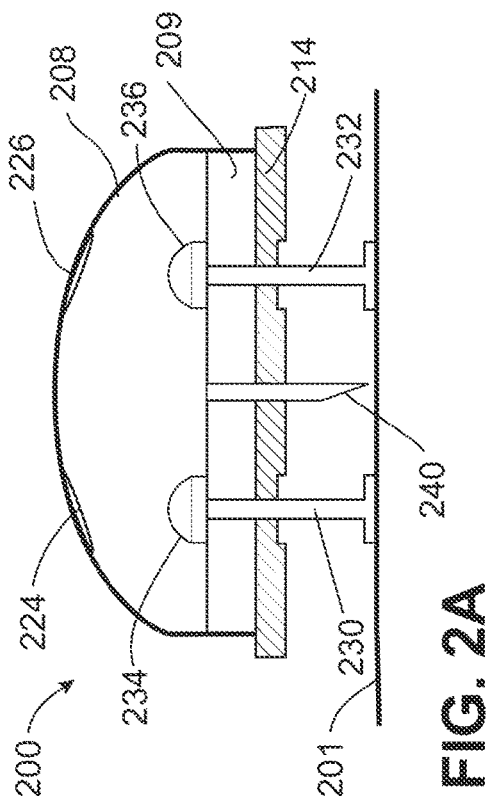

A further embodiment according to the invention is shown in FIG. 2A and FIG. 2B, wherein at least a pair of mechanical posts 230, 232 is positioned proximate cannula 240, on opposite sides of cannula 240. The posts are preferably located at a distance of less than 12 mm from the cannula, catheter or probe, as the case may be, to prevent the device registering as fully inserted when skin 201 at the injection site is tented away from base 214 of housing 208.

Posts 230, 232 move proximally in housing 208 as cannula 240 is inserted. The cannula (or catheter as the case may be) may be inserted by pressing the housing against the insertion site or by providing an automated insertion mechanism, as is also practiced in the diabetes care art. In the example shown, insertion monitor 200 comprises base 214 and top 208. Cannula 240 is supported in hub 209 and has a beveled end protruding distally from base 214 for insertion into a subject's skin. Posts 230, 232 protrude from base 214 as housing 208 is placed in position, and when base 214 is flush against the skin, the posts are preferably arranged so that the distal surfaces of posts 230, 232 are flush with base 214. As cannula 240 is inserted into the skin, the posts travel proximally within the housing in correspondence with insertion of the cannula. This proximal movement of posts 230, 232 is controlled by the engagement of posts 230, 232 in hub 209, as well as by movement of housing 208 and base 214 toward the injection site. For this purpose, posts 230, 232 are made of rigid material, such as metal or molded polypropylene (PP), or molded acrylonitrile butadiene styrene (ABS) so that the posts move proximally toward the top of the housing as the base becomes situated adjacent the skin. Whereas base 214 may be made flexible to conform to a wearer's body, posts 230, 232 maintain a vertical position, parallel to the cannula, as a result of engagement with hub 209.

When cannula 240 reaches full insertion depth, the proximal ends of posts 230, 232 are visible through windows 224, 226 in the top of the housing. Alternatively, or in addition, as shown schematically in FIG. 2B, mechanical posts 230, 232 may make contact with respective surfaces 225, 227 in the housing when the cannula reaches full penetration depth. Surfaces 225, 227 may be electrical contacts which may close one or more circuits in sensor circuit 216 to generate an alert mechanism indicating that cannula 214 is at full penetration depth, transmitted visibly or audibly to the user or generating an electronic signal to a peripheral device such as a glucose monitor or infusion pump. Alternatively, contacts 234, 236 may cause a polymeric color change material to undergo a visible color change to provide indication through windows 224, 226 that cannula 240 has reached full penetration depth. Likewise, when the cannula is not properly seated at the insertion site, contact is interrupted between the surface in the housing and the posts, and a different audible or visual indication may be generated to alert the user. Depending on the application, information may be transmitted to peripheral components of the system, for example, to stop an infusion (in the context of a pump or patch having a remote component), or to stop testing (in the context of a remotely located glucose monitor or infusion pump).

Where one of the pair of posts 230, 232 contacts a surface 225, 227, but not the other, this may indicate an angled insertion status, which may be used to generate a visible and/or audible alert using LEDs 229 or audible alarm 223, or may be used to generate a signal transmitted to a remote device indicating a likely angled insertion status.

Figure 2C:
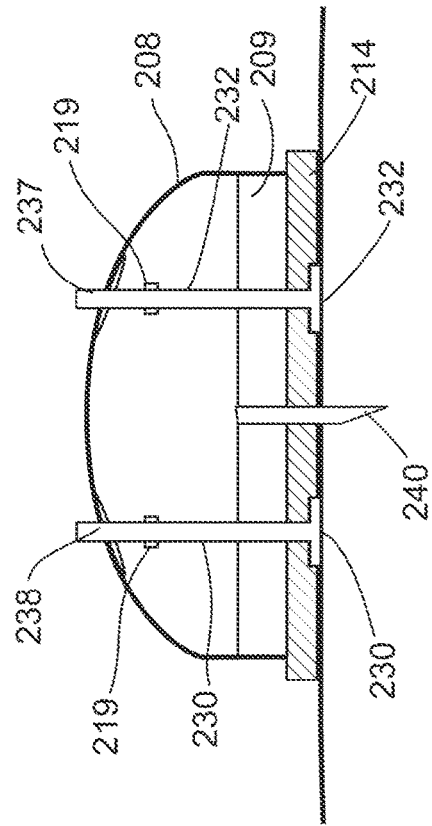
Figure 2D:
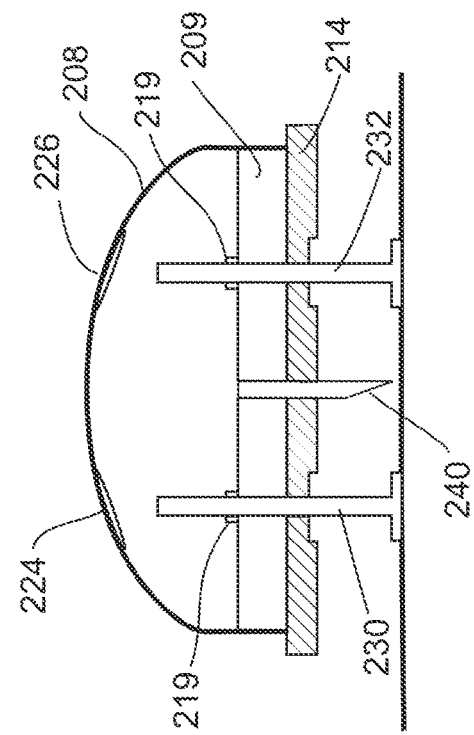

In the embodiment of FIG. 2C and FIG. 2D, posts 230, 232 provide a tactile indication for the user that the cannula has reached full penetration depth. This is particularly useful, for example, if the housing 208 is positioned out of sight, on a back portion of the abdomen, for example. In this embodiment, posts 230, 232 protrude from the top of the housing 208 through windows 224, 226 and the user can feel the protruding tips to ensure that the cannula is fully seated at the insertion site. Stops 219 are provided to engage posts 230, 232 in hub 209 to control movement of the posts and prevent posts 230, 232 from separating from hub 209.

Figure 3C:
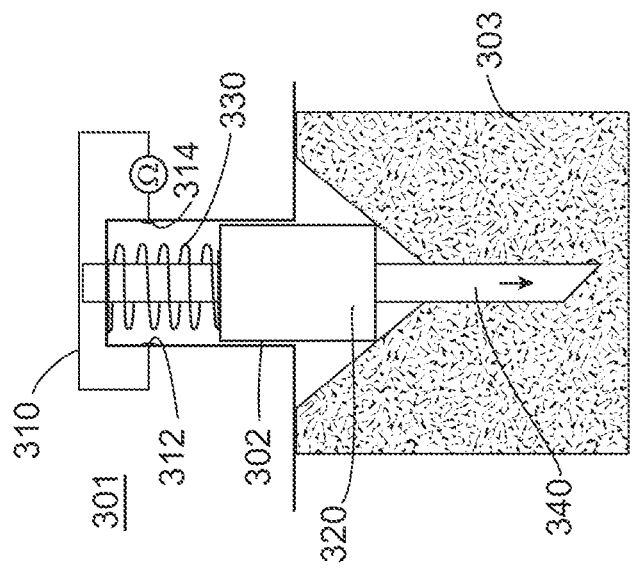
FIG. 3A, FIG. 3B and FIG. 3C depict a cannula insertion monitor according to another embodiment of the invention, utilizing a spring loaded collar surrounding a cannula.
Figure 3B:
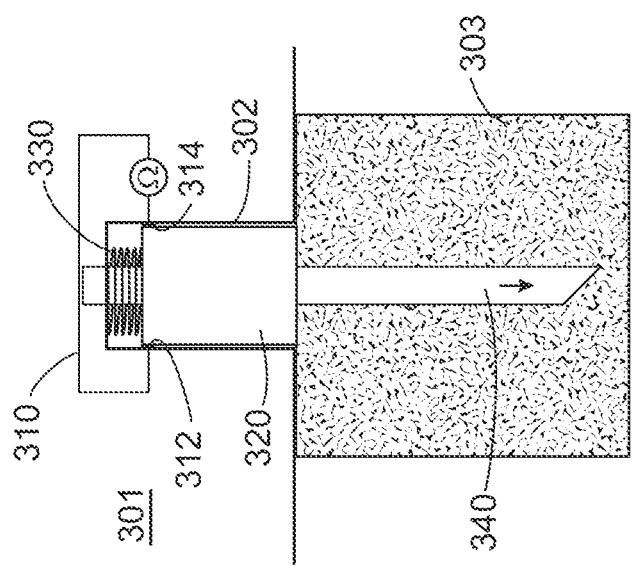
Figure 3A:
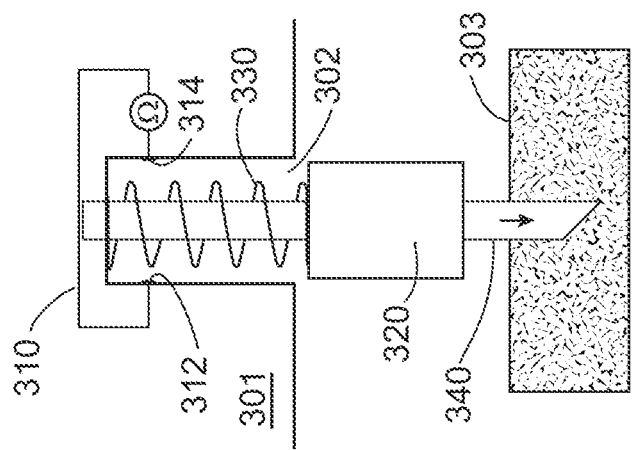

Still another embodiment of the invention is depicted in FIG. 3A, FIG. 3B and FIG. 3C, to detect whether a cannula, catheter or probe is inserted to its full depth with respect to the surface of the skin. As with the other embodiments, the device of this embodiment may be used to alert a continuous glucose monitor (CGM) user (or other device user) user to a poorly inserted cannula in the on-body sensor (OBS) (or other device component). This embodiment comprises a spring loaded, sliding collar concentric with the cannula such that, before OBS insertion, it protrudes beyond the plane of the bottom of the device. Upon proper, full depth insertion of the cannula, the plane of the OBS bottom will contact the plane of the skin, pushing the collar into a recessed space in the OBS base. When the recess is occupied, an electrical, magnetic, or optical detector detects the occupied state of the recess and delivers a positive signal to a display or to the electronics and software systems of the remote sensor or drug delivery system, as the case may be. If the skin does not fully contact the housing base (as in a state of "tenting", wherein the skin does not return to being flat after cannula penetration), the collar will not occupy the recess and no signal will be generated.

In the embodiment of FIGS. 3A, 3B, and 3C housing 301 contains a recess 302 which receives collar 320 sliding on cannula 340. Although described in connection with a cannula, the person of ordinary skill in the art would recognize that the system could as well be adapted to insertion detection of a catheter. In the embodiment shown, collar 320 is urged distally under the bias of compression spring 330. Cannula 340 is supported in the housing 301, preferably using a hub (not shown), as generally known and understood in the art, and as described in connection with the previous embodiments.

FIG. 3B depicts the state wherein collar 320 is fully seated in recess 302, so that the distal side of collar 320 is aligned with the distal side of the housing and positioned adjacent the user's skin 303. In the embodiment shown, electrical contacts 312 and 314 are closed when the collar is seated in the recess, sending a signal via circuit 310 that the cannula 340 is fully inserted. In this way, a glucose monitor or infusion pump can receive a signal to commence or restart operation. Alternatively, or in addition, the 'ready" status of cannula insertion may be indicated audibly or visually using LED or audible alarm or combination thereof, as in the previous embodiments. In other embodiments, instead of electrical contacts 312 and 314, an optical or magnetic sensor may be used.

FIG. 3A depicts a first example in which cannula 340 may not be fully inserted into the injection site. In this state, compression spring 330, which is used to urge the collar against the user's skin, is fully extended so that collar 320 is not seated in recess 302. This state is detected by contacts 312, 314 (or other sensor system), and an alert mechanism is triggered to peripheral user interface devices. FIG. 3C depicts a second example similar to FIG. 3A in which a disruption in the plane of the subject's skin caused by tenting results in the failure of the cannula collar 320 to be seated in recess 302. The state of cannula insertion in these cases is indicated by an appropriate alert, generated via LED or audible alarm, or by transmitting a signal to a peripheral device, such as a glucose monitor or infusion pump, regarding the "not ready" status of the cannula.

Figure 4A:
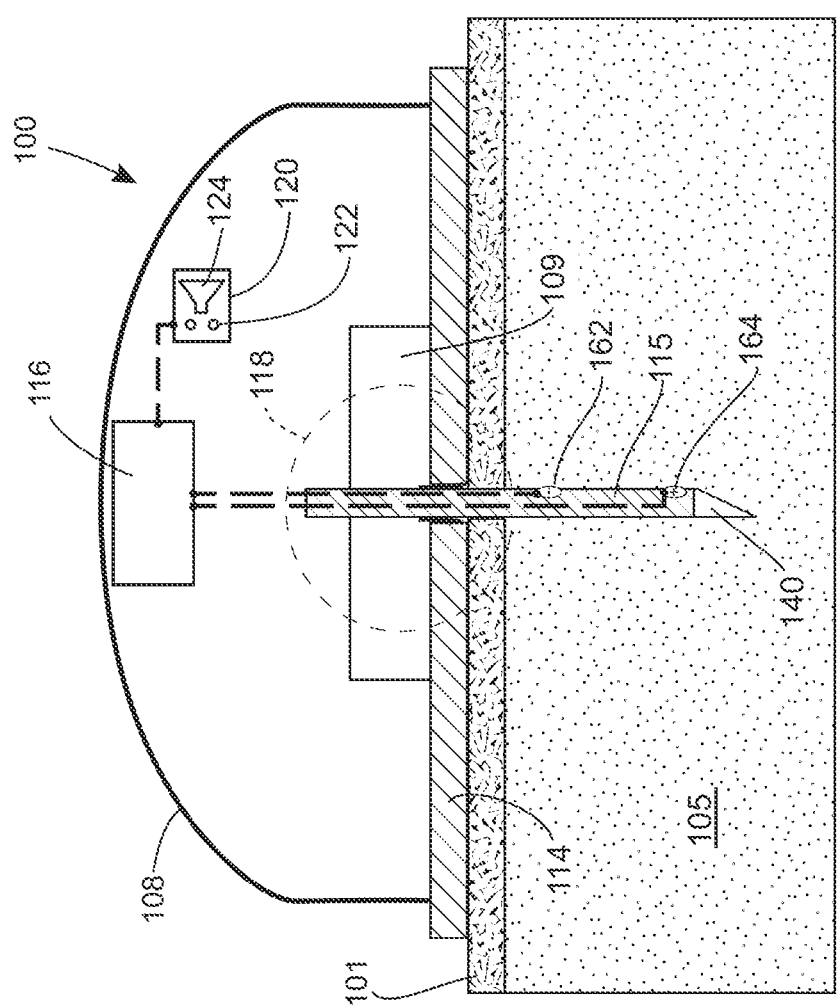
FIG. 4A and FIG. 4B depict a cannula insertion monitor according to another embodiment of the invention, utilizing electrodes on the cannula or catheter itself.
Figure 4B:
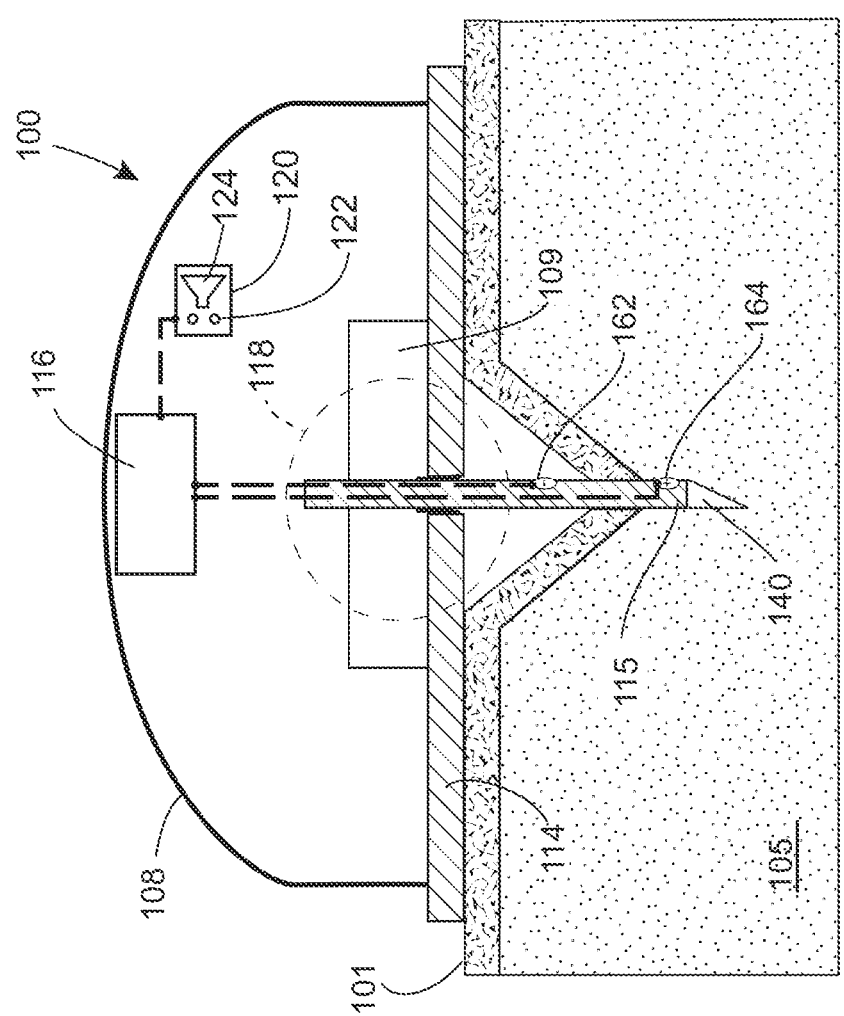

The embodiment of FIG. 4A and FIG. 4B is similar to the embodiment of FIG. 1 except that electrical contacts are placed on the cannula and changes in conductive properties of the skin or interstitial fluid detected by the contacts are used to determine injection status of the cannula. As in the earlier embodiment, housing 108 (which could be part of a glucose monitoring on-body sensor, or an infusion set or pump) comprises a base 114 positioned against the user's skin 101 at a site where cannula 140 is to be inserted and cannula 140 is supported on hub 109. Cannula 140 is provided with an insulating layer 115, and electrically conductive distal electrode 164 and proximal electrode 162 are positioned on insulating layer 115. As seen in FIG. 4A, when cannula 140 is fully inserted in the subject's skin, electrodes 164 and 162 are both within an interstitial space having a generally defined conductivity due to the relatively high concentration of electrolytes in the interstitial fluid. A current in sensor circuit 116 flows between the electrodes. If the cannula is not inserted fully, as in FIG. 4B, as when the plane of the skin is distorted due to tenting, for example, then the proximal electrode 162 will not enter the interstitial space 105, and conductivity between the electrodes 162, 164 will be affected in a predictable direction. Likewise, if the cannula is initially properly inserted but is then disturbed, a sudden change in conductivity will occur.

When a change in conductivity between electrodes 162 and 164 occurs, the status of the circuit detected in the sensor circuit 116 may be transmitted to peripheral user interface devices, for example, triggering an alarm to alert the user that the device is not inserted properly in the skin. In the case of a glucose monitor, for example, a signal indicating sufficient conductivity between electrodes 162, 164 may be made a necessary condition for glucose monitoring to commence or restart. If the device is a medication delivery device, the insertion monitor may trigger, stop or interrupt medication delivery. Alternatively, audible alarm 124 or visible indicator such as LEDs 120 may be used to provide the user with an indication of cannula insertion status. Sensor circuit may detect and evaluate an electrical property other than conductivity to obtain information about the status of the cannula insertion. Determining capacitance between electrodes 162, 164, for example, when cannula 140 is fully inserted and not fully inserted may correlate to cannula insertion status.

In the foregoing embodiments, the cannula or probe inserted in the subject's tissue is preferably stainless steel. The resistive layer 115 and electrode layers 162, 164 may be deposited on the cannula by means known in the art, including chemical vapor deposition (CVD), plasma enhanced chemical vapor deposition (PECVD), printing, and like methods.

In a case were the stainless steel cannula itself serves as an electrode, the cannula may be rolled or brushed with resistive ink, leaving a selected area near the bevel conductively exposed to the subject's body. Cannula 140 can then be paired with another electrode on housing 108 and an electrical property between the electrode on the housing and cannula 140 is detected by sensor circuit 116 and correlated with cannula insertion status.

The foregoing description of the preferred embodiments is not to be deemed limiting of the invention, which is defined by the appended claims. The person of ordinary skill in the art, relying on the foregoing disclosure, may practice variants of the embodiments described without departing from the scope of the invention claimed. For example, although largely described in connection with blood glucose monitoring and continuous delivery of insulin for treatment of diabetes, it will be apparent to those of skill in the art that the infusion pump could be adapted to deliver other medications and the monitor adapted to test for another analyte. A feature or dependent claim limitation described in connection with one embodiment or independent claim may be adapted for use with another embodiment or independent claim, without departing from the scope of the invention. For example, cannula insertion detection may be used advantageously in the case where a cannula is inserted manually by the user pushing on the housing, and equally well in the case where a cannula is propelled into the user's tissue by automated injection.

What is claimed is:

1. An insertion monitor, comprising:
a housing adapted to be positioned on a subject's skin adjacent an insertion site, and having a recess receiving a spring loaded collar, and receiving a cannula, catheter or probe;
the cannula, catheter or probe having a distal end with a sharpened tip and a proximal end fixed in the housing;
the spring loaded collar comprising a collar surrounding the cannula, catheter or probe, and a spring positioned between the recess in the housing and the collar for sliding the collar along the cannula, catheter or probe under bias of the spring;
a sensor detecting when the spring loaded collar is seated fully in the recess in the housing with a distal surface of the collar in a plane with a distal surface of the housing; and
an alert mechanism triggered when the sensor detects cannula, catheter or probe insertion status.

2. The insertion monitor according to claim 1, wherein said spring surrounds the cannula, catheter or probe.

3. The insertion monitor according to claim 1, wherein the sensor detects the position of said collar with respect to said housing to sense the insertion status of the cannula, catheter or probe.

4. The insertion monitor according to claim 1, wherein said housing comprises electrical contacts in said recess, and where said electrical contacts are closed when said collar is seated fully in said recess and said cannula, catheter, or probe is fully inserted, and where said collar does not close said electrical contacts when the subject's skin is tented around the cannula, catheter or probe and said collar is not seated fully in said recess.

5. The insertion monitor according to claim 1, wherein the sensor is optical, magnetic or electrical.

6. The insertion monitor according to claim 1, wherein the sensor is optical, magnetic or electrical, and the alert mechanism includes an audible alarm on the housing.

7. The insertion monitor according to claim 1, wherein the sensor is optical, magnetic or electrical, and wherein the alert mechanism includes a transmitter sending a signal to a device remote from the insertion site.

8. The insertion monitor according to claim 1, wherein the insertion site is remote from an infusion pump or a blood glucose monitor.

\* \* \* \* \*